(12) United States Patent
Rapin et al.

(10) Patent No.: US 7,129,213 B2
(45) Date of Patent: Oct. 31, 2006

(54) TRIPEPTIDES AND TRIPEPTIDE DERIVATIVES FOR THE TREATMENT OF NEURODEGENERATIVE DISEASES

(75) Inventors: Jean Rapin, Paris (FR); Hans Klaus Witzmann, Egglkofen (DE); Jean-Marie Grumel, Tassin la Demi-Lune (FR); Jacques Gonella, Muttenz (CH)

(73) Assignee: Neurotell AG, Hergiswil (CH)

( * ) Notice: Subject to any disclaimer, the term of this patent is extended or adjusted under 35 U.S.C. 154(b) by 0 days.

(21) Appl. No.: 10/635,797

(22) Filed: Aug. 5, 2003

(65) Prior Publication Data
US 2005/0101538 A1 May 12, 2005

Related U.S. Application Data (63) Continuation of application No. PCT/EP02/01180, filed on Feb. 5, 2002.

(51) Int. Cl.
| A61K 38/00 | (2006.01) |
| A61K 38/06 | (2006.01) |
| C07K 5/00 | (2006.01) |
| C07K 7/00 | (2006.01) |
| C07K 16/00 | (2006.01) |
| C07K 17/00 | (2006.01) |
| C07K 38/00 | (2006.01) |

(52) U.S. Cl. ..................................... 514/18; 530/331
(58) Field of Classification Search .................. 514/18; 530/330, 331, 338
See application file for complete search history.

(56) References Cited

U.S. PATENT DOCUMENTS

| 5,091,391 | A | * | 2/1992 | Aizenman et al. ........... 514/311 |
| 5,212,158 | A | | 5/1993 | Vandai |
| 5,804,563 | A | * | 9/1998 | Still et al. ...................... 514/26 |
| 5,840,838 | A | * | 11/1998 | Hensley et al. .............. 530/324 |
| 5,973,111 | A | | 10/1999 | Bemis et al. |
| 6,080,848 | A | * | 6/2000 | Henrichwark et al. ...... 536/23.5 |
| 6,156,572 | A | | 12/2000 | Bellamkonda et al. |
| 6,235,929 | B1 | * | 5/2001 | Powers ......................... 562/450 |
| 6,846,641 | B1 | * | 1/2005 | Wieloch et al. ............. 435/7.21 |

FOREIGN PATENT DOCUMENTS

| EP | 0316218 A1 | | 5/1989 |
| EP | 0445606 A1 | * | 9/1991 |
| EP | 0446706 A2 | | 9/1991 |
| EP | 0446706 A3 | | 9/1991 |
| EP | 10818341 A | | 7/2000 |
| EP | 1231279 A1 | | 8/2002 |
| JP | 04-005240 A | | 1/1992 |
| JP | 09040577 | * | 2/1997 |
| JP | 09169797 | * | 6/1997 |
| WO | WO 88/09604 A2 | | 12/1988 |
| WO | WO 92/11850 A2 | | 7/1992 |
| WO | WO92/13549 | * | 8/1992 |
| WO | WO 96/41638 A1 | | 12/1996 |
| WO | WO 98/14202 A1 | | 4/1998 |
| WO | WO 01/28578 A2 | | 4/2001 |
| WO | WO 01/28578 A3 | | 4/2001 |
| WO | WO 01/34828 A1 | | 5/2001 |
| WO | WO 01/68114 A1 | | 9/2001 |
| WO | WO 02/062373 A2 | | 8/2002 |
| WO | WO 02/062373 A3 | | 8/2002 |
| WO | WO 02/062828 A2 | | 8/2002 |
| WO | WO 02/062828 A3 | | 8/2002 |

OTHER PUBLICATIONS

Kan. Current and future approaches to therapy of Alzheimer's disease. Eur J Med Chem. 1992, vol. 27, pp. 565-570.*
Hofman et al. Atherosclerosis, apolipoprotein E, and prevalence of dementia and Alzheimer's disease in the Rotterdam Study. Lancet 1997, vol. 349, pp. 151-154.*
Scientists uncover Alzheimer's clues. BBC News, Sunday Jun. 25, 2000. (Accessed online May 3, 2005 at http://news.bbc.co.uk/1/hi/health/803297.stm) pp. 1-3.*
Beyer, H., and Walter, W., *Handbook of Organic Chemistry*, by S. Hirzel Verlag, Stuttgard (English translation of the 22$^{nd}$ edition of *Lehrbuch der Organischen Chemie*) (1996), pp. 827-838.
Blundell, T.L., et al., "Knowledge-based protein modelling and design", *Eur. J. Biochem.*, 172:513-520 (1988).
Chessebeuf, M., et al., "Rat liver epithelial cell cultures in a serum-free medium: primary cultures and derived cell lines expressing differentiated functions", *In Vitro*, 20(10):780-795 (1984).
Clark, M.C., et al., "Validation of the general purpose Tripos 5.2 force field", *J. Comp. Chem.*, 10(8):982-1012 (1999).
De Pooter, H., et al., "N-acylamino acids and peptides IV the synthesis of N-cinnamyl-, N-p.coumaryl- and N-caffeyl-glycine and -glycyl-L-phenylalanine", *Bull. Soc. Chim. Belg.*, 85(9):647-656 (1976). XP008015013.

(Continued)

Primary Examiner—Cecilia J. Tsang
Assistant Examiner—Marcela M Cordero Garcia
(74) Attorney, Agent, or Firm—Madeline I. Johnston, Esq.; King & Spalding, LLP (57) ABSTRACT

The invention relates to the use of specific tripeptides for the treatment of neurodegenerative diseases, and to pharmaceutical compositions comprising the tripeptides. The tripeptide derivatives satisfy the following formula (I): wherein X represents OH, $(C_{1-5})$ alkoxy, $NH_2$, $NH$—$C_{1-5}$-alkyl, $N(C_{1-5}$ alkyl$)_2$; $R_1$ is a residue derived from one of the amino acids Phe, Tyr, Trp, Pro, which each may be optionally substituted with one or more $(C_{1-5})$alkoxy groups, $(C_{1-5})$alkyl groups or halogen atoms, as well as Ala, Val, Leu or Ile; $R_2$ is a residue derived from one of the amino acids Gly, Ala, Ile, Val, Ser, Thr, Leu and Pro; $Y_1$ and $Y_2$ independently from each other represent H or $(C_{1-5})$alkyl; $R_3$ and $R_4$ independently from each other represent H, OH, $(C_{1-5})$alkyl or $(C_{1-5})$alkoxy, provided that $R_3$ and $R_4$ are not both OH or $(C_{1-5})$alkoxy; and $R_5$ represents H, OH, $(C_{1-5})$alkyl or $(C_{1-5})$alkoxy; or a pharmaceutically acceptable salt thereof.

14 Claims, 1 Drawing Sheet

OTHER PUBLICATIONS

Faden, A.I., et al., "Novel TRH analog improves motor and cognitive recovery after traumatic brain injury in rodents", *Amer. J. Physiology* 277(4, pt. 2):R1196-R1204 (1999), *Chem. Abstr.* 132:31033 XP002207513, XP008014976.

Faden, A.I., et al., "Structure-activity relationships of TRH analogs in rat spinal cord injury", *Brain Research*, 448:287-293 (1988). XP008015202.

Gasteiger, J., et al., "Iterative partial equalization of orbital electronegativity—a rapid access to atomic charges", *Tetrahedron*, 36:3219-3238 (1980).

Hagg, T., et al., "Delayed treatment with nerve growth factor reverses the apparent loss of cholinergic neurons after acute brain damage", *Exp. Neurol.*, 101:303-312 (1988).

Jones, D.T., et al., "A new approach to protein fold recognition", *Nature*, 358:86-89 (Jul. 1992).

Jones, D.T., "Protein secondary structure prediction based on position-specific scoring matrices", *J. Mol. Biol.*, 292(2):195-202 (1999).

Kansy, M., et al. "Physicochemical High Throughput Screening: Parallel Artificial Membrane Permeation Assay in the Description of Passive Absorption Processes", *J. Med. Chem.*, 41(7):1007-1010 (Mar. 26, 1998).

Khuebachova, M., et al., "Mapping the C terminal epitope of the Alzheimer's disease specific antibody MN423", *J. Immunol. Methods* (*Elsevier Amsterdam, NL*) 262(1-2):205-215 (2002), XP004352190.

Laskowski, R.A., et al., "Procheck: a program to check the stereochemical quality of protein structures", *J. Appl. Cryst.*, 26:283-291 (1993).

Le Poncin-Lafitte, M., et al., "Sound-avoidance conditioning and a mathematical approach to the description of acquisition performance", *Math. Biosciences*, 59:249-268 (1982).

Luco, J.M., "Prediction of the brain-blood distribution of a large set of drugs from structurally derived descriptors using partial least-squares (PLS) modeling", *J. Chem.. Inf. Comput. Sci.*, 39 (2):396-404 (1999).

Parnetti, L., et al., "Posatirelin for the treatment of late-onset Alzheimer's disease: a double-blind multicentre study vs citicoline and ascorbic acid", *Acta Neurol. Scand.* 92:135-140 (1995).

Varon, S., et al., "Nerve Growth Factor in CNS Repair", *J. Neurotrama*, 11(5) (1994).

Wang, R., et al., "SCORE: A new empirical method for estimating the binding affinity of a protein-ligand complex", *J. Mol. Model.*, 4:379-394 (1998).

Weiner, S.J., et al., "A new force field for molecular mechanical simulation of nucleic acids and proteins", *J. Am. Chem. Soc.*, 106:765-784 (1984).

Wiesman, C., et al., "Crystal structure of nerve growth factor in complex with the ligand-binding domain of the TrkA receptor", *Nature*, 401:184 (Sep. 9, 1999).

Faden, A.I., et al., "Effect of TRH analogs on neurologic recovery after experimental spinal trauma," *Neurology*, 35:1331-1334 (1985).

Geschwind, M., et al., "Detection of apoptotic or necrotic death in neuronal cells by morphological, biochemical, and molecular analysis," in *Apoptosis Techniques and Protocols*, J. Poirier, ed., 1997, pp. 13-31.

Guiloff, R.J., "Thyrotropin releasing hormone and motorneurone disease", *Reviews in the Neurosciences*, 1:201-219 (1987).

Kurtz, A.F., "Praktische Diagnostik, in *Aktuelles Wissen Hoechst, Alzheimer-Patienten erkennen und behandeln*," Hoechst AG, publisher (Munich, Germany, 1995), 68-69. *With partial translation*.

Rapin, J.R., "Les nootropes: propriétés pharmacologiques du piracétam et indications thérapeutiques," *La Lettre du Pharmacologue*, 6(5):108-111 (1992). *With partial translation*.

Sarti, G., et al., "TRH-analogues: A possible treatment for symptoms of dementia in elderly patients?", *Archives of Gerontology and Geriatrics*, 12:173-177 (1991).

Szirtes, T., et al., "Synthesis of thyrotropin-releasing hormone analogues. 1. Complete dissociation of central nervous system effects from thyrotropin-releasing activity," *J. Med. Chem.* 27:741-745 (1984).

\* cited by examiner

Fig. 1/1: Correlation between experimental and calculated brain-blood-distribution based on 15 descriptors.

TRIPEPTIDES AND TRIPEPTIDE DERIVATIVES FOR THE TREATMENT OF NEURODEGENERATIVE DISEASES

This application is a continuation, under 35 U.S.C. §365 (c), of the PCT patent application entitled "Tripeptides and Tripeptide Derivatives for the Treatment of Neurodegenerative Diseases," having International Application No. PCT/EP02/01180, International Filing Date of 5 Feb. 2002 (May 02, 2002), and Priority Date of 5 Feb. 2001 (May 02, 2001), which claims priority to German Patent Application No. 101 05 041.0, filed on 5 Feb. 2001, the disclosures of which are entirely incorporated herein by reference.

The invention relates to the use of tripeptides and tripeptide derivatives for the treatment of neurodegenerative diseases, particularly Alzheimer's disease and mild cognitive impairment, and to pharmaceutical compositions comprising tripeptides or tripeptide derivatives and a pharmaceutically acceptable carrier.

BACKGROUND ART

Neurodegenerative diseases are characterised by a degradation or degeneration of nerves which are generally caused by apoptosis. Examples of neurodegenerative diseases include Alzheimer's disease, mild cognitive impairment, Parkinson's disease as well as AIDS-related neurological disorders. For example, in Alzheimer's disease, the nerve degradation leads to a disruption of the ability to remember, speak, think and make decisions. The reasons for these disorders are not known in detail. On the biochemical level, a change in the cortical cholinergic systems with a decrease in the formation of the neurotransmitter acetylcholine is detectable. In the cerebral cortex of patients suffering from Alzheimer's disease, the acetylcholine concentration is decreased by 20 to 40%. As a result thereof, nerve ends are attacked, and this leads ultimately to the death of the cerebral cells, particularly those of the hippocampus.

In light of these observations, therapeutic approaches for Alzheimer's disease therefore address the stabilisation of the acetylcholine concentration, particularly by inhibiting acetylcholine esterase which degrades acetylcholine to acetate and choline. However, the use of acetylcholine esterase inhibitors shows the drawback that this results in an only temporary improvement which is not suitable for stopping or even reversing the nerve degeneration.

On the other hand, so-called neurotrophic factors or neurotrophines are known to which a significant influence on the survival, growth and differentiation of discrete neuronal populations is ascribed. The neurotrophine family includes nerve growth factor (NGF), brain derived neurotrophic factor (BDNF), neurotrophine-3 (NT-3), neurotrophine-4 (NT-4) and the CNTF-family (ciliary neurotrophic factor). Neurotrophines are small basic proteins with a molecular weight of 26 to 28 kDa. NGF is the best characterised member of the neurotrophine family which shows activity in many different tissues.

In the peripheral nervous system (PNS) NGF is critical to the development of sympathetic and certain sensory nerves. In the central nervous system (CNS), NGF serves a trophic role in the development and maintenance of cholinergic neurons of the basal forebrain. It also plays a role in adult CNS tissues in neuronal regeneration.

It is known that cholinergic neurons produce acetylcholine in the presence of NGF rather than in its absence. Moreover, it has also been demonstrated that the administration of NGF to primates leads to the regeneration of cholinergic cell bodies. Based on this finding it is assumed that an altered activity of NGF may thus be a starting point for the degeneration of cholinergic neurons. At least theoretically it thus appears that neurotrophic substances are suitable for the treatment of neurodegenerative diseases such as Alzheimer's disease. However, these physiologically occurring substances have a short action radius similar to autocrine or paracrine substances. Therefore it is until today not possible to use common therapeutical routes (enteral or parenteral) for their application, as they are processed proteolytically in the blood circulation and other tissues and are thereby inactivated. Besides, it is known that they do not pass the blood-brain barrier (BBB) which is a prerequisite of CNS activity.

Clinical trials carried out with recombinant human neurotrophines have failed so far. A conceivable intracerebral administration should be excluded by practical consideration. Therefore, a transfer of results from in vitro experiments with NGF or other neurotrophines, as well as with fragments of these peptides, to a possible therapeutic application is not possible.

SUMMARY OF THE INVENTION

Hence, it is the object of the present invention to provide specific substances which lead to a stopping and preferably reversing of nerve degeneration, particularly of hippocampus cells, and which are also suitable for common therapeutic administration thus allowing their use as medicament for the treatment of neurodegenerative diseases. Moreover, it is an object of the present invention to provide corresponding pharmaceutical compositions.

This object of the present invention is solved by the use of compounds of the following formula (I):

wherein X represents OH, $(C_{1-5})$alkoxy, $NH_2$, $NH$—$C_{1-5}$-alkyl, $N(C_{1-5}$ alkyl$)_2$;

$R_1$ is a residue derived from one of the amino acids Phe, Tyr, Trp, and Pro, which each may be optionally substituted with one or more $(C_{1-5})$alkoxy groups, $(C_{1-5})$alkyl groups or halogen atoms, as well as Ala, Val, Leu or Ile;

$R_2$ is a residue derived from one of the amino acids Gly, Ala, Ile, Val, Ser, Thr, Leu, and Pro;

$Y_1$ and $Y_2$ independently from each other represent H or $(C_{1-5})$alkyl;

$R_3$ and $R_4$ independently from each other represent H, OH, $(C_{1-5})$alkyl or $(C_{1-5})$alkoxy, provided that $R_3$ and $R_4$ are not both OH or $(C_{1-5})$alkoxy; and $R_5$ represents H, OH, $(C_{1-5})$alkyl or $(C_{1-5})$alkoxy;

or a pharmaceutically acceptable salt thereof;

for the preparation of a medicament useful in the treatment of neurodegenerative diseases.

The pharmaceutical composition of the present invention comprises compounds of the above formula (I), wherein X represents OH, $(C_{1-5})$alkoxy, $NH_2$, $NH$—$(C_{1-5})$-alkyl, $N(C_{1-5}$ alkyl$)_2$;

$R_1$ is a residue derived from the amino acid Phe which may be optionally substituted with one or more $(C_{1-5})$alkoxy groups, $(C_{1-5})$alkyl groups or halogen atoms;

$R_2$ represents a residue derived from one of the amino acids Gly, Ala, Ile, Val, Ser, Leu, Thr;

$Y_1$ and $Y_2$ independently from each other represent H or $(C_{1-5})$alkyl;

$R_3$ and $R_4$ independently from each other represent H, OH, $(C_{1-5})$alkyl or $(C_{1-5})$alkoxy, provided that $R_3$ and $R_4$ do not both represent OH or $(C_{1-5})$alkoxy; and $R_5$ represents H, OH, $(C_{1-5})$alkyl or $(C_{1-5})$alkoxy;

or a pharmaceutically acceptable salt thereof, and a pharmaceutically acceptable excipient.

DETAILED DESCRIPTION

If not indicated otherwise, the amino acid residues may be present both in the D-form as well as the L-form, the L-form being preferred.

Preferred are compounds of the formula (I) in which $R_1$ is a residue derived from the amino acid Ile or one of the amino acids Phe, Tyr, Trp, which each may be optionally substituted with one or more $(C_{1-5})$alkoxy groups, $(C_{1-5})$ alkyl groups or one or more halogen atoms, particularly a residue which is derived from Ile or Phe which is optionally substituted with one or more $(C_{1-5})$alkoxy groups, $(C_{1-5})$ alkyl groups or one or more halogen atoms.

In formula (I), X is preferably $(C_{1-5})$alkoxy, $NH_2$, NH—$(C_{1-5})$alkyl or $N(C_{1-5}$ alkyl$)_2$, more preferred are $NH_2$, $NH(C_{1-3})$alkyl and $N(C_{1-3}$ alkyl$)_2$.

$R_2$ is preferably a residue derived from the amino acid Gly or Ile.

$R_3$ and $R_4$ preferably independently from each other represent H, $(C_{1-5})$alkyl or $(C_{1-5})$alkoxy, provided that $R_3$ and $R_4$ are not both OH or $(C_{1-5})$alkoxy, more preferred are H, $(C_{1-3})$alkyl or $(C_{1-3})$alkoxy.

$R_5$ preferably represents H, $(C_{1-5})$alkyl or $(C_{1-5})$alkoxy, particularly preferred are H, $(C_{1-3})$alkyl or $(C_{1-3})$alkoxy.

$Y_1$ and $Y_2$ preferably independently from each other represent H or $(C_{1-3})$alkyl.

For particularly preferred compounds of formula (I), $R_1$ is a residue which is derived from Phe which is optionally substituted with one or more $(C_{1-5})$alkoxy groups, $(C_{1-5})$ alkyl groups or one or more halogen atoms, or which is derived from the amino acid Ile, $R_2$ is a residue derived from the amino acid Gly or Ile, $R_3$, $R_4$ and $R_5$ represent a hydrogen atom, X is $NH_2$, NH—$(C_{1-3})$alkyl or $N(C_{1-3}$ alkyl$)_2$, and $Y_1$ and $Y_2$ independently from each other represent H or $(C_{1-3})$alkyl.

Most preferred compounds of formula (I) are glycyl-L-phenylalanyl-L-prolineamide, N,N-diethyl-isoleucyl-phenylalanyl-L-proline ethylamide, N,N-diethyl-isoleucyl-isoleucyl-prolineamide or a pharmaceutically acceptable salt thereof.

The abbreviations used for the amino acids (Phe for phenylalanine etc. as well as partially the one-letter-codes used below, such as F for phenylalanine) are known to the skilled person (see e.g. Beyer and Walter, Lehrbuch der Organischen Chemie, 21st edition, S. Hirzel Verlag Stuttgart 1988). Hence, Phe means phenylalanine, Gly glycine etc. The expression "a residue derived from the amino acid Phe" thus means a benzyl (—$CH_2$—$C_6H_5$) residue. Accordingly, "a residue derived from the amino acid Gly" means a hydrogen atom, "a residue derived from the amino acid Ala" a methyl group etc.

The compounds of formula (I) used according to the present invention are water soluble substances and are thus suitable for enteral or parenteral administration.

However, the compounds used according to the present invention are not all equally suitable for oral/enteral or parenteral administration. For example, whereas HCl-Gly-Phe-ProNH$_2$ is considered mainly for parenteral administration, N,N-Diethyl-Ile-Ile-ProNH$_2$ and N,N-Diethyl-Ile-Phe-ProNHEt are suitable for parenteral and particularly oral administration. The suitability of the compounds to be used according to the present invention for oral administration can be estimated using the so-called Parallel Artificial Membrane Permeation Assay which is described in more detail below. For oral administration, those compounds having values of more than 10, preferably more than 30, more preferably more than 45, as determined according to this assay, are preferred.

An essential prerequisite for the effectivity of the tripeptides and tripeptide derivatives used according to the present invention is their concentration in the CNS. Besides other factors, this is affected by the extent of the passage of the blood-brain barrier which may take place by active or passive transport. A so-called facilitated transport or transport via lipid rafts is considered as mechanisms. The balance of the transport is expressed independently from its type or mechanism by the blood-brain distribution coefficient (log BB). The higher this coefficient, the higher is the concentration in the CNS.

The definition and determination of the brain-blood distribution coefficient by molecular modelling in connection with QSAR (quantitative structure activity relationships) is described in more detail below. The blood-brain distribution coefficient of the compounds to be used according to the present invention is preferably −3,5 or higher, particularly preferred being one in the range of −3,0 and higher.

Furthermore, the substances of formula (I) used according to the present invention show a high affinity to tyrosine kinase receptors (TrkA, TrkB, and TrkC). Since the neurotrophic substance NGF is known to act via docking to these receptors, a high affinity to the receptors is a strong indication of the neurotrophic action of the compounds used according to the present invention. The docking constants (pKD) may be determined by molecular modelling tools, and a corresponding method is described in more detail below. The compounds used according to the present invention have preferably pKD-values of 5.5 or more, even more preferred are pKD-values of 7 or more.

The synthesis of the tripeptides and tripeptide derivatives used according to the present invention is not particularly limited and can be carried out according to known methods, preferably stereo-specific processes of peptide chemistry in which the L- or D-configuration of the respective amino acids or their derivatives is maintained. Various peptide syntheses are described in Beyer and Walter, Lehrbuch der Organischen Chemie, 21st edition, S. Hirzel Verlag Stuttgart 1988, pages 829–834. Preferred methods include the N-carboxylic acid anhydride method (NCA-method) and the method using mixed carboxylic acid anhydrides, as illustrated by the following reaction equations:

NCA-method:

1.

2.

3.

4.

Mixed carboxylic acid anhydride synthesis:

1.

2.

3.

4.

5.

wherein AA1 and AA2 represent the middle and terminal amino acids (derived from $R_1$ or $R_2$) respectively, Boc represents a tert-butyloxycarbonyl residue, NCA represents N-carboxylic acid anhydride and TFA represents trifluoro acetic acid. The starting materials are commercially available.

When using amino acids having functional groups, such as e.g. serine, it is possible to protect these in a manner known to the skilled person.

Moreover, the tripeptides or tripeptide derivatives used according to the present invention may be synthesised in optionally modified Merryfield synthesis on a solid phase, preferably using fluoren-9-yl-methoxy-carbonyl protective groups (Fmoc residues) or Fmoc/tert-butyl (tBu) protected amino acids.

The reactions described above have yields of generally more than 90%, with respect to the individual reaction steps, and a total yield of more than 60%. The purity of the thus synthesised tripeptides and tripeptide derivatives is generally more than 98% and is thus sufficient for the use in pharmaceutical compositions. The structures of the tripeptides and tripeptide derivatives may be confirmed by mass spectroscopy (MS), high pressure liquid chromatography (HPLC), automated amino acid analysis (AAA), optical rotation (OR), and/or infrared and ultraviolet spectroscopy (IR, UV).

An administration in a dose of more than 5 mg per kilogram bodyweight per day is usually effective, particularly in multiple parenteral administration.

Due to their molecular structure these substances show a very low toxicity both in acute and chronic toxicity tests. The smallest lethal dose (i.v.) in rats was 250 to 350 mg per kilogram bodyweight. Hence, the tested substances show a convenient therapeutical ratio which is a prerequisite for a therapeutical use in humans.

The tripeptides or tripeptide derivatives may be used for the production of pharmaceutical compositions which are suitable for administration in different ways, e.g. parenteral (intravenous, intramuscular, subcutane), via the respiratory tract (buccal, sublingual, nasal, bronchial), the transdermal route (percutane) and the enteral route (peroral). In the latter case, a suitable dosage is necessary to overcome the first pass effect.

The pharmaceutical compositions of the present invention further contain a pharmaceutically acceptable excipient, pharmaceutically acceptable diluents or adjuvants. Standard techniques may be used for their formulation, as e.g. disclosed in Remington's Pharmaceutical Sciences, $20^{th}$ edition Williams&Wilkins, PA, USA.

The administration form is selected depending on the administration route and comprises inter alia tablets, capsules, powders and solutions.

For oral administration, tablets and capsules are preferably used which contain a suitable binding agent, e.g. gelatine or polyvinyl pyrrolidone, a suitable filler, e.g. lactose or starch, a suitable lubricant, e.g. magnesium stearate, and optionally further additives.

A particularly preferred formulation for oral administration is a coated tablet containing 100 mg or 200 mg N,N diethyl-Ile-Ile-ProNH$_2$, silicon dioxide, magnesium stearate, Macrogol 400/600, Hypromellose (E404) titanium dioxide, and croscarmellose-Na.

For parenteral administration, sterile aqueous solutions are preferred. Suitable aqueous solvents include water, physiological saline solution, Hank solution und Ringer solution. Preferred is inter alia a physiological saline solution containing 20 g/l of the tripeptides or tripeptide derivatives, e.g. glycyl-L-phenylalanyl-L-prolineamide.

A particularly preferred formulation for parenteral administration is an ampul for injection containing 5 ml–10 ml of injection solution for infusion comprising 100 mg or 200 mg of lyophilized Gly-Phe-ProNH$_2$, acetic acid, sodium acetate, and water for injection.

The anti-neurodegenerative effect of the tripeptides or tripeptide derivatives used according to the present invention is surprising since peptides are usually subject to proteolytic degradation by endo- or exopeptidases and further metabolisation, so that it could not be expected that they reach and even pass the blood-brain barrier. The extent and the rate of this degradation is indicated by the half lifetime of the tripeptide or tripeptide derivative in plasma. It is known that the half-life period of tripeptides such as e.g. thyreoliberin (TRH) is very short. Therefore, it is surprising that the tripeptides and tripeptide derivatives used according to the present invention show an unexpectedly long half-life period ($\geq 24$ h). This long half-life period is a further prerequisite for a sufficient anti-neurodegenerative effect.

Moreover, in experiments with hepatocytes, it could be shown experimentally that the tripeptides and tripeptide derivatives of the present invention are only slowly metabolised in the liver. This result was confirmed by analysis of the plasma and of the added hepatocytes in which only the unaltered tripeptide or tripeptide derivative was analyzed was used after an exposition of four hours and more.

The superior therapeutic properties of the tripeptides and tripeptide derivatives used according to the present invention will be further illustrated below using particularly useful models for Alzheimer's disease. Using these models, it could be demonstrated that the administration of the tripeptides or tripeptide derivatives used according to the present invention does not only result in an increase of the number of hippocampal neurons, but also results in an improvement of the learning capacity of the rats used in the tests. However, before describing these experiments in detail, the determination of the blood-brain distribution coefficient, the PAMPA assay, the determination of the TrK-docking constants, the determination of the metabolic stability and selected syntheses of the tripeptide derivatives used in the subsequent experiment is described.

Experimental Section

1. Determination of the Brain-Blood Distribution Coefficient

As noted above, the blood-brain barrier generally presents an obstacle for water soluble substances impeding the use of many water soluble substances for the treatment of the CNS by common administration. However, it could be demonstrated that the tripeptides or tripeptide derivatives used according to the present invention show the capability of passing said blood-brain barrier. The blood-brain distribution of the tripeptides and tripeptide derivatives used according to the present invention may be quantified as follows.

The so-called QSAR (quantitative structure activity relationship) technique is an established technique for the quantification of specific physicochemical or pharmacological properties of chemical compounds. This technique generally comprises the determination of a linear correlation between a specific experimental property of the compounds (such as e.g. the brain-blood distribution coefficient (BB)) with calculated structural parameters A, B, C etc. by modulation of the so-called descriptors (X1, X2, etc.), generally resulting in an equation of the following form:

Log $BB=(X1 \times A)+(X2 \times B)+(X3 \times C)+ \ldots +$ constant

With the thus obtained descriptors it is then possible to calculate the respective experimental properties, such as e.g. the brain-blood distribution coefficient, of compounds for which no experimental data is available. Accordingly, the brain-blood distribution is determined as follows according to the present invention.

On the basis of experimental data of 75 compounds (see Luco, J. M., J. Chem. Inf. Comput. Sci. (1999), 39, 396–404) and specific parameters, as explained in the following, a linear correlation between calculated and experimental values could be obtained.

The compounds were constructed using the molecular modelling programme package SYBYL (Tripos Associates Inc., 1699 S. Henley Road, Suite 303, St. Louis, Mo. 63144, USA). To determine low energy conformations of the compounds for a selected set (A-F-P, A-dF-P, A-F-dP, A-dF-dP) a random search was performed. All dehedral angles, except those of the peptide bond, were considered flexible. The backbone conformations of the structures with the lowest energy were taken as the starting conformation for all compounds.

All manually constructed compounds were energetically minimised using the Tripos force fields (see Clark, M., Kramer, III, R. D. and van Optenbosch, N. (1989), J. Comp. Chem. 10, 982–991) with Gasteiger (PEOE) partial charges (Gasteiger, J., Marsili, M. (1980; Tetrahedron 36, 3219–3238)) and a distant-dependent dielectric constant of 4.

The molecular graphics programme MOE (Chemical Computing Group Inc., Montreal, Canada, http://www.chemcomp.com) allows the calculation of a widely applicable set of descriptors depending only on the connectivity of the compounds and the atom types (types in the sense of force field parameters) (see Labute on the home page cited above). All descriptors used herein include a simple approximation of the van der Walls surface of the compounds. For the test set of 1947 organic compounds, a high correlation ($r^2=0.9666$) resulted between the exact van der Walls surface and the 2D approximation. The first set of 14 parameters (PEOE-VSA) considered the charge distribution (PEOE) of the molecule using uniform interval boundaries. A second set of 10 descriptors (SlogP-VSA) describes the log (P) of the compounds and a third set of 8 (SMR-VSA) depend on molecular polarisability.

Figure 1:
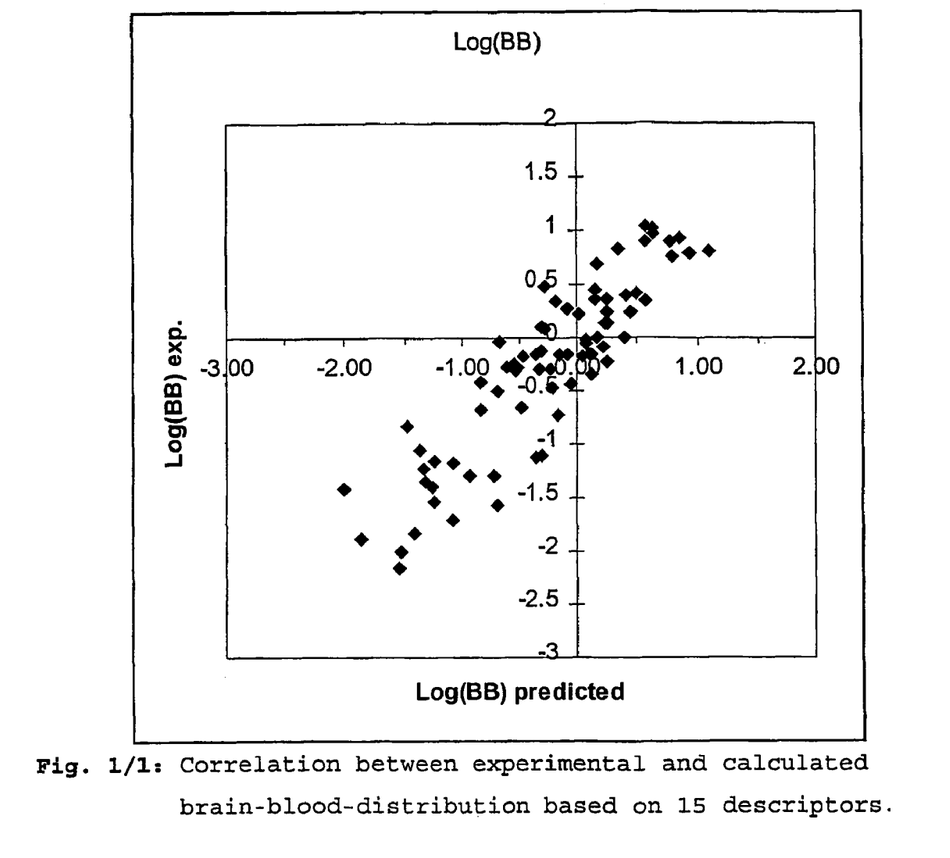
FIG. 1 shows the correlation of experimental and calculated values of the blood brain distribution

The values of all 32 descriptors described above were calculated for each of the 75 compounds (see Lucco, J. M., J. Chem. Inf. Comput. SCI. (1999), 39, 396–404) in order to find a correlation to the experimental brain-blood distribution. A principal components' regression has been performed to estimate a linear model of Log (BB) as a function of the descriptors. In the first calculation it appeared that 8 descriptors could be neglected due to very low contribution. After the second run without these 8, a further 9 descriptors with contributions less than 0.1 appeared. Finally, based on the calculations of 70 compounds (5 obvious outliers were removed) using the remaining 15 descriptors, a relatively good linear, as well as cross-validated (leave-one-out) correlation resulted. This correlation is graphically represented in FIG. 1 (in this graphic: used components: 15; condition number 663.7658; root mean square error (RMSE): 0,20126; correlation coefficient (R2): 0,03240; cross-validated R2: 0,88321).

Log (BB) is defined as follows:

LOG (BB)=Log(concentration in the brain)/(concentration in blood).

The descriptors obtained by this correlation could then be used for the calculation of the blood-brain distribution of the tripeptides and tripeptide derivatives of the present invention.

Inter alia, the following values were obtained which relate to the forms present in the physiological pH range:

| $A_1$ and $A_1$ derivates | $A_2$ and $A_2$ derivates | $A_3$ and $A_3$ derivates | brain-blood distribution coefficient |
| --- | --- | --- | --- |
| G | F | POH | −4.9 |
| G | F | $PNH_2$ | −3.3 |
| G | F | $PN(Et)_2$ | −3.3 |
| G | F | POEt | −2.8 |
| L | F | $PNH_2$ | −2.0 |
| G | D-F | $PNH_2$ | −3.3 |
| G | F | D-$PNH_2$ | −3.3 |
| A | P | $PNH_2$ | −3.1 |
| A | P | 3,3-di-Me—$PNH_2$ | −2.3 |
| I | P | 3,3-di-Me—$PNH^2$ | −2.1 |
| $N(Et)_2$-G | I | $PNH_2$ | −2.0 |
| $N(Et)_2$-I | I | $PNH_2$ | −1.6 |
| I | I | $PNH_2$ | −2.6 |
| I | S | $PNH_2$ | −3.5 |
| I | 3,4,5-tri-MeO—F | $PNH_2$ | −3.5 |
| I | 3,4-di-Me—F | $PNH_2$ | −2.7 |
| G | W | $PNH_2$ | −3.8 |
| G | Y | $PNH_2$ | −3.9 |

$A_1$: aliphatic amino acids including substitution at the amino group, corresponding to formula (I) $Y_1Y_2N$—$CR_2H$—CO—.
$A_2$: aromatic amino acids including substitution on the phenyl ring as well as aliphatic amino acids, according to formula (I) —NH—$CHR_1$—CO—.
$A_3$: proline and derivatives
D: dextro rotatory The following conclusions may be drawn from these calculations:

(a) The use of prolineamide, proline(diethyl)amide and the prolinemethylesters instead of the free acid of proline is preferred with regard to the passage of the blood-brain barrier.

(b) Among the structural units of $A_2$ (corresponding to $R_1$ of formula (I)), the aromatic amino acid F and alkyl derivatives thereof as well as isoleucine (I) are preferred.

(c) Among the structural units $A_1$ (corresponding to $R_2$ of formula (I))), the aliphatic amino acid I as well as the substitution of the amino group of G and I with 2 ethyl groups are particularly preferred.
(d) The optical chirality of the amino acid units does apparently not play a role at least for the passive passage of the blood-brain barrier.

2. Gastrointestinal Absorption

The absorption of an orally administered drug is determined by its ability to cross the gastrointestinal barrier. The Parallel Artificial Membrane Permeation Assay system (PAMPA) is a simple and fast method for the prediction of gastrointestinal drug absorption. Drug permeation of biological cell layers is mainly related to passive diffusion processes. The PAMPA method measures the permeation of potential new drugs across an artificial membrane by passive diffusion and allows a classification into low, medium and high absorbers.

The procedure according to the Parallel Artificial Membrane Permeation Assay described by Kansy et al. was used (Kansy M., Senner F., Gobernator K., Physicochemical High Throughout Screening: Parallel Artificial Membrane Permeation Assay in the Description of Passive Absorption Processes, J. Med. Chem., 1998, 41(7), 1007–1010). The artificial membrane was built up by pipetting a solution of lecithine in organic solvent on a supporting filter material in 96-well plates. For all test compounds, stock solutions of 5 mM were prepared in ethanol. They were then diluted in Tris-buffer (0.05 M, pH 7,4) to a final concentration of 500 µM. Permeation rates of all test compounds were measured in triplicate or quadruplicate. Diffusion time across the artificial membrane was 16 h. For all compounds reference values without phospholipid layer were individually determined. Concentrations in the acceptor compartments were measured by UV difference spectroscopy using a microtiter plate reader Spectramax Plus[384] from Molecular Devices. For each compound the λmax values were determined in a previous run and measurements were performed at this wavelength. The permeation rates are expressed as flux rates, which are calculated according to the following formula: flux (%)=OD (test well)/OD (control well)×100. As internal standards, 3 drugs with known flux rates for low, medium and high permeation were included in the test plate: Bretylium, Hydrocortisone and Coumarin. After the permeation experiment, an integrity check of the membrane was performed to examine whether the test compounds injured the artificial membrane by a toxic or unspecific effect, and therefore constituting a false positive result. Lucifer Yellow, a non-permeating dye, has been applied to each well postexperimentally and the concentration of the marker measured in a Wallac Victor[2] 1420 Multilabel Counter. Wells, in which the concentration of Lucifer Yellow exceeded 1% of the amount detected in the control wells (without artificial membrane) were discarded. In the present experiment only one well (for the reference compound Bretylium) exceeded this limit and was therefore not taken into account.

Table 1 shows the flux rates of the 7 test compounds and the 3 reference compounds.

| Compounds | Pampa Flux (%) Mean ± SEM | Number of wells |
|---|---|---|
| HCl-Gly-Phe-ProNH$_2$ | 0 | 4 |
| TRH | <10 | 4 |
| N,N-Diethyl-Ile-Ile-ProNH$_2$ | 47 ± 1 | 4 |
| N-Isopropyl-Ile-Ile-ProNH$_2$ | 35 ± 1 | 3 |
| N,N-Diethyl-Gly-Ile-ProNH$_2$ | 25 ± 0.5 | 3 |
| N,N-Diethyl-Ile-Phe-ProNHEt | 51 ± 6 | 4 |
| H-Gly-Phe-Pro-OH | 0 | 4 |
| Bretylium | 0 | 2 |
| Hydrocortisone | 55 ± 1 | 4 |
| Coumarin | 72 ± 2 | 4 |

The internal control constituted by 3 reference compounds, the flux rates of which have been measured several times by us and others (see Kansy et al. above), have shown no abnormalities and attest the good conditions in which the experiment was performed. Bretylium, an actively transported compound, which shows a low bioavailability in humans, exhibited a flux rate of 0% in this experiment as well. The flux rates for Hydrocortisone and Coumarin, published by Kansy et al. (see above) were 52 and 66%, respectively. These data are in very good accordance to the results we obtained in our experiment (Table 1).

The PAMPA method allows a classification of compounds into 3 groups:

Low (flux rate <20%), medium (20%<flux rate <50%) and high (flux rate >50%) permeators. According to this classification, HCl-Gly-Phe-ProNH$_2$, as well as TRH and H-Gly-Phe-Pro-OH will be weakly absorbed compounds, N,N-Diethyl-Ile-Ile-ProNH$_2$, N-Isopropyl-Ile-Ile-ProNH$_2$, N,N-Diethyl-Gly-Ile-ProNH$_2$ and N,N-Diethyl-Ile-Phe-ProNHEt are predicted to be medium to highly absorbed compounds after peroral application.

Based on the results obtained in this study, the following ranking of the test compounds for the permeability of biological membranes can be made:

HCl-Gly-Phe-ProNH$_2$, H-Gly-Phe-Pro-OH<TRH, N,N-Diethyl-Gly-Ile-ProNH$_2$<N-Isopropyl-Ile-Ile-ProNH$_2$<N,N-Diethyl-Ile-Ile-ProNH$_2$<N,N-Diethyl-Ile-Phe-ProNHEt A limitation of the PAMPA permeation test system as it is described here, is the fact that it can only detect compounds, which are transported by the transcellular route. Compound, which prefer the paracellular or active route might give low flux rates despite a good absorption in humans after peroral application.

3. Determination of Docking Constants

Based on X-ray structure or models of dimer fragments of TrkA, TrkB and TrkC, docking studies of several compounds of formula (I) were performed. For all the arrangements of the ligands between both monomers their affinity constants (pKd=pKi) should be calculated by means of theoretical methods (see Wang, R.; Liu, L., Lai, L., Tang, Y., J. Mol. Model., 1998, 4, 379–394).

a) Modelling of the Dimer Arrangement of the Receptors

The basis for all the following investigations is the X-ray structure (pdb=1 www) of a TrkA fragment docked by NGF (see Wiesmann, C., Ultsch, M. H., Bass, S. H., De Vos, A. M., Nature 1999, 401, 184).

We suppose that the ligands may bind in a similar way as NGF to two monomers of TrkA, TrkB or TrkC. The higher the affinity of the ligands, the closer both monomers will be held together, which is considered as the main function for activity. Since NGF is much larger than the tripeptide derivatives, models have to be formed which allow binding of the rather small molecules. For this purpose the coordinates of NGF were removed from the X-ray structure and one monomer was moved manually close to van der Walls contact to the other monomer (using the molecular modelling package SYBYL (TRIPOS Associates Inc.). To find a relevant arrangement of both unoccupied monomers together molecular dynamics simulations (MD) using the AMBER-ALL-ATOM force field (see S. J. Weiner et al., J. Amer.Chem.Soc. 1984, 106, 765–784) at 150 K for 20000 fs were carried out. The resulting structure after this simulation was optimised to an energy gradient of 0.1 kcal/mol Å2. This structure was used as template to model the structures of TrkB and TrkC as well as for docking studies.

Models of the dimer arrangement of TrkB and TrkC were generated by using the homology modelling tool COMPOSER (see Blundell, T. L., Carney, D., Gardner, S., Hayes, F., Howlin, B., Hubbard, T., Eur.J.Biochem. 1988, 172–513–20) of SYBYL and subsequent MD and energy minimisations. The resulting structures were checked for quality using PROCHECK (see Laskowski, R. A., MacArthur, M. W., Moss, D. S., Thornton, J. M., J. Appl.Cryst., 1993, 26, 283–91).

b) Docking Studies of the Ligands

The program GOLD [See Jones, D. T., J.Mol.Biol., 1999, 292(2), 195–202; Jones, D. T., Taylor, W. R., Thornton, J. M., Nature 1992, 358, 86–89)] was used for "automatic" docking of the ligands. To ensure optimal docking for each of the ligands to all three receptors, two slightly different binding sites were investigated. Using GOLD for each run 20 docking structures (altogether 40) were determined. Since the protein structures are considered to be fixed, all 40 arrangements were optimised keeping only the back bone of the receptor fixed.

c) Determination of the Affinity Constants

For all protein-ligand complexes the interaction energies of the ligands with the receptors were calculated using the Tripos force field, the so-called fitness values using GOLD and the program SCORE [see Wang et al, ibid] to determine pKd-values which correspond to pKi-values in case of enzyme inhibitor complexes (the higher the fitness or pKd values the higher is the affinity of the ligands). SCORE considers not only interaction energies but also salvation, desolvation and entropy effects in the docking arrangements.

The results are summarised in the following table showing the best pKd (pKi)-values for each of the ligands to a receptor. The table also shows the values of the brain blood distribution as determined above.

The highest affinity was predicted for Et2-IFP-NH-Et (pKi-value of 7.29 (about 100 nM) when binding to TrkA (by SCORE). Some hydrogen bonds can be detected, however, most important are hydrophobic interactions of both N-terminal ethyl groups as well as of the Ile side chain with three histidine residues and of the phenylalanine side chain with Phe327 of the receptor. For all the remaining ligands the affinity is about one order of magnitude less.

| Ligand | Receptor | pKd value | Log BB |
| --- | --- | --- | --- |
| HCl-Gly-Phe-ProNH$_2$ | TrkC | 6.15 | −3.3 |
| N,N-Diethyl-Ile-Ile-ProNH$_2$ | TrkB | 6.15 | −1.7 |
| N-Isopropyl-Ile-Ile-ProNH$_2$ | TrkA | 6.31 | −2.2 |
| N,N-Diethyl-Gly-Ile-ProNH$_2$ | TrkA | 5.44 | −2.0 |
| N,N-Diethyl-Ile-Phe-ProNHEt | TrkA | 7.29 | −2.4 |
| H-Gly-Phe-Pro-OH | TrkC | 5.58 | −4.9 |

4. Syntheses a) Synthesis of HCl—H-Gly-L-Phe-L-Pro-NH$_2$

Step 1: Boc-L-Phe-OH+H-L-Pro-NH$_2$→Boc-L-Phe-L-Pro-NH$_2$ 87.6 g Boc-L-Phe-OH was dissolved in a mixture of 50 ml dimethylformamide (DMF) and 300 ml 1,2-dimethoxyethane (DME) and cooled to −15° C. Subsequently, 37 ml N-methylmorpholine (NMM) (1 equivalent) was added at once and subsequently 45 ml isobutylchloroformate (IBCF) (1 equivalent) was added dropwise over 10 min. The mixture was then stirred for further 5 min at −15° C. 40 g TFA.H-L-Pro-NH$_2$ (1.06 equivalents) was subsequently added in portions over 5 min, and then 315 ml N,N-diisopropyl-N-ethylamine (DIEA) (1 equivalent) was added at once. The reaction mixture was reacted over night at room temperature and atmospheric pressure. Subsequently, the reaction mixture was concentrated in a rotatory evaporator equipped with a water aspirator and a dry ice/acetone trap, and the residue was taken in 1 l of ethylacetate followed by twelve washes with 80 ml 1N aqueous KHSO$_4$ solution, one wash with 80 ml brine, ten washes with 80 ml saturated aqueous NaHCO$_3$ solution, one wash with 80 ml brine in a 2 l separatory funnel. The subsequent drying was carried out over 50 g Na$_2$SO$_4$. After filtration through a sinter glass funnel (coarse porosity) was concentrated as described above. The residue of evaporation (dry foam) was then triturated in 1 l hexane, and a solid was collected on a sinter glass funnel (120 mm i.d.×120 mm, medium porosity). This was followed by drying in a desiccator over 12 hours at room temperature and a pressure of 0.1 to 1 mm Hg (vacuum oil pump, with dry ice/acetone trap). Thus, 92.8 g Boc-L-Phe-L-Pro-NH$_2$ was obtained (yield: 77.8%).

Analytical Data:

| | |
| --- | --- |
| molar mass (mass spectroscopy): | 317 g/mol |
| melting point: | 60° C. (decomposition) |
| purity (HPLC): | 95.2% |
| optical rotation [Na/20° C.]: | −23.9 |
| H$_2$O [KF]: | 1.84% |
| heavy metals: | 25.4 ppm |
| solvents: | 2.02 ‰ |
| element analysis: | 64.0% C |
| | 7.4% H |
| | 11.4% N |
| | 17.0% O |

Step 2: Boc-L-Phe-L-Pro-NH$_2$→TFA.H-L-Phe-L-Pro-NH$_2$

Boc-L-Phe-L-Pro-NH$_2$ (180 g) obtained in step 1 were dissolved/suspended in 250 ml methylene chloride in a 2 l round-bottom flask, equipped with a magnetical stirrer. Then, 250 ml of trifluoro acetic acid was reacted with the solution at room temperature (15–25° C.) and atmospheric pressure for one hour. The reaction mixture was then precipitated in 5 l tert-butylmethyl ether (TBME) under stirring. The precipitate was collected on a sinter glass funnel and subsequently washed twice with 1.5 l diethyl ether and twice with 1 l hexane. The subsequent drying was carried as described above in step 1.

Step 3: Boc-Gly-OH+TFA.H-L-Phe-L-Pro-NH$_2$→Boc-Gly-L-Phe-L-Pro-NH$_2$ 44 g Boc-Gly-OH (1 equivalent) was dissolved in a mixture of 50 ml DMF and 300 ml DME and subsequently cooled to −15° C. 28 ml NMM (1 equivalent) was added at once, followed by the dropwise addition of 34 ml IBCF (1 equivalent) over 10 min. The mixture was stirred a further 5 min at −15° C. 94.5 g TFA.H-L-Phe-L-Pro-NH$_2$ (1.06 equivalents) were added in portions thereto over 5 min, followed by the addition of 44 ml DIEA (1 equivalent). The reaction mixture was reacted over night at room temperature and atmospheric pressure. Subsequently, the reaction mixture was concentrated in a rotatory evaporator, equipped with a water aspirator and a dry ice/acetone trap, and the residue was taken in 1.2 l ethyl acetate, followed by five washes with 80 ml 1N aqueous KHSO$_4$ solution, five washes with 80 ml saturated aqueous NaHCO$_3$ solution, and one wash with 80 ml brine in a 2 l separatory funnel. The subsequent drying was carried out over 50 g Na$_2$SO$_4$. After filtration through a sinter glass funnel (coarse porosity) concentration was carried out as described above. The residue of evaporation (sticky oil) was then triturated in a mixture of 1 l diethyl ether and 2 l hexane and a solid was collected on a sinter glass funnel (180 mm i.d.×180 mm, medium porosity). The subsequent drying was carried out in a desiccator over 12 hours at room temperature and a pressure of 0.1 to 1 mm Hg (vacuum oil pump, with dry ice/acetone trap). Accordingly, 100 g Boc-Gly-L-Phe-L-Pro-NH$_2$ was obtained (yield: 94.7%).

Analytical Data:

| | |
|---|---|
| molar mass (mass spectroscopy): | 418 g/mol |
| melting point: | 66° C. (decomposition) |
| purity (HPLC): | 98.6% |
| optical rotation [Na/20° C.]: | −27.9 |
| H$_2$O [KF]: | 3.78% |
| heavy metals: | 40.2 ppm |
| solvents: | 1.8 ‰ |
| element analysis: | 61.2% C |
| | 7.5% H |
| | 12.8% N |
| | 18.4% O |

Step 4: Boc-Gly-L-Phe-L-Pro-NH$_2$→HCL.H-Gly-L-Phe-L-Pro-NH$_2$

Boc-Gly-L-Phe-L-Pro-NH$_2$ (149 g) obtained in step 3 were dissolved/suspended in 300 ml methylene chloride and then 300 ml 4N HCl/dioxane was added at once. The mixture was reacted for one hour at room temperature (15–25° C.) at atmospheric pressure in a 2 l round-bottom flask equipped with a magnetical stirrer. Subsequently, 1 l diethyl ether was added to the reaction mixture and the precipitate was collected on a sinter glass funnel. The precipitate was then washed twice with 1.5 l diethyl ether and dried as described in step 1.

Analytical Data:

| | |
|---|---|
| molar mass (mass spectroscopy): | 318 g/mol |
| melting point: | 93° C. (decomposition) |
| purity (HPLC): | 98.8% |
| optical rotation [Na/20° C.]: | −19.1 |
| H$_2$O [KF]: | 2.79% |
| heavy metals: | 15.9 ppm |
| solvents: | 0.72 ‰ |
| element analysis: | 53.7% C |
| | 6.4% H |
| | 14.3% N |
| | 14.9% O | b) Synthesis of N,N-Diethyl-Ile-Phe-Pro-NH-Et

N,N-Diethyl-Ile-Phe-Pro-NH-Et acetate was prepared by solid phase synthesis as follows:

| Step | Reaction | Reagent | Time | Temperature |
|---|---|---|---|---|
| 0 | H-R + Fmoc-Phe-OH→ Fmoc-Phe-R (I) | B | 2.00 h | 20° C. |
| 1 | (I) →H-Phe-R (II) | A | 0.25 h | 20° C. |
| 2 | (II) +Boc-Ile-OH→ Boc-Ile-Phe-R (III) | B | 12.00 h | 20° C. |
| 3 | (III) →H-Ile-Phe-Pro-NH-Et (IV) | C | 1.50 h | 20° C. |
| 4 | (IV) →Separation by HPLC (IV) | D | | 20° C. |
| 5 | (IV) →N,N-Diethyl-Ile-Phe-Pro-NH-Et (V) | DMF, ethylbromide | | |
| 6 | (V) →Separation by HPLC (V) | D | | 20° C. |
| 7 | (V) →Lyophilisation (V) | | | 20° C. |
| 8 | (V) →Formation of Acetate (VI) | E | | 20° C. |
| 9 | (VI) → Lyophilisation (VII) store at −20° C. | | | −20° C. |

H-R: H-Pro-(SASRIN)-N-Et (proprietory of Bachem AG, CH; on polystyrene basis)
A: 20% Piperidine in DMF
B: DCCl/HOBt/DMF
C: 95% TFA, thereafter evaporation
D: RP-HPLC on C18, System: 0.1% TFA/Acetonitrile
E: anion exchanger in the acetate form, elution with water Analytical Data:
Appearance: Yellowish product
Solubility: 1 mg/ml in 5% acetic acid (clear, colorless solution)
Amino Acid Analysis: Pro 1.00 (1)
Phe 0.03 (1)
Ile 0.01 (1)
N,N diethyl-Ile cannot be determined;
Ile-Phe bond incomplete hydrolysis
ESI-MS: m=458.5 u (average mass)
Purity (HPLC): >95%
Water content: 3.9%

Synthesis of N,N-Diethyl-Ile-Ile-Pro-NH-Et

N,N-Diethyl-Ile-Ile-Pro-NH-Et acetate salt was prepared by solid phase synthesis as follows:

| Step | Reaction | Reagent | Time | Temperature |
|---|---|---|---|---|
| 0 | Fmoc-R → H-R (I) | A | 0.25 h | 20° C. |
| 1 | (I) + Fmoc-Ile-Pro-OH → Fmoc-Ile-Pro-R (II) | B | 1.25 h | 20° C. |
| 2 | (II) → H-Ile-Pro-R (III) | A | 0.25 h | 20° C. |

-continued

| Step | Reaction | Reagent | Time | Temperature |
|------|----------|---------|------|-------------|
| 3 | (III) +Fmoc-Ile--OH → Fmoc-Ile-Ile-Pro-R (IV) | B | 1.50 h | 20° C. |
| 4 | (IV) → H-Ile-Ile-Pro-R (V) | A | 0.25 h | 20° C. |
| 5 | (V) → H-Ile-Ile-Pro-NH$_2$ (VI) + HO—R | C | 1.50 h | 20° C. |
| 6 | (VI) → N,N-Diethyl-Ile-Ile-Pro-NH$_2$ (VII) | DMF, ethylbromide | | |
| 7 | (VII) → Separation by HPLC (VII) | D | | 20° C. |
| 8 | (VII) → Lyophilisation (VII) | | | 20° C. |
| 9 | (VII) → Formation of Acetate (VIII) | E | | 20° C. |
| 10 | (VIII) →Lyophilisation (VIII) store at −20° C. | | | −20° C. |

Fmoc-R = Fmoc-Ramage-Resin (D-2200) Fmoc-Ile-Pro-OH (B-2135), Fmoc-Ile-OH (B-1340)
A = 20% Piperidine in DMF
B = TBTU/DIPEA/DMF
C = 95% TFA, thereafter precipitation with IPE
D = RP-HPLC on C$_{18}$, System: 0.1% TFA/Acetonitrile
E = Anion Exchanger in the acetate form, Elution with H$_2$O Analytical Data:
   Appearance: Yellowish product
   Solubility: 1 mg/ml in water (clear, colorless solution)
   Amino Acid Analysis: Pro 1.00 (1)
   Ile 0.03 (1)
   N,N-diethyl-Ile cannot be determined;
   Ile-Ile bond incomplete hydrolysis
   ESI-MS: m=396.5 u (average mass)
   Purity (HPLC): >96%
   Water content: 2.0%

5. Determination of Metabolic Stability

Isolation and Culture of Rat Hepatocytes

Hepatocytes from adult male Wistar rats (IFFA Credo, L'Arbresle, France) were isolated by an in situ liver perfusion using collagenase (purchased from Sigma (St. Louis, Mo., U.S.A), according to a procedure described by Seglen (Preparation of isolated rat liver cell, Methods Cell Biol. 13, 29–83, 1976) and modified by Williams et al. (Rat hepatocyte primary culture. III. Improved dissociation and attachment techniques and the enhancement of survival by culture medium, in vitro 13: 809–817, 1977). After estimation of cell viability by the peripheral refractoriness of intact cells in phase contrast microscopy and the trypan blue test, freshly isolated hepatocytes were washed in basal William's medium E (WME) supplemented with 10% (v/v) fetal calf serum, 70 μM cortisol, 2 mM L-glutamine, 10 mM HEPES buffer, and 4 mM NaOH. They were then plated at a density of 0.5×10$^6$ cells per 50 mm plastic cell culture dishes in the medium described previously for cell attachment for 6 hours at 37° C. Subsequently, hepatocytes were washed three times in serum- and cholesterol-free medium (SF-WME) containing 4 g/l bovine albumin fraction V (Sigma) as transporter for 7.8 μM of a mixture of free fatty acids (Cheesebeuf M and Padieu P, expression of major liver metabolic function in long-term serum-free rat liver epithelial cell lines. In vitro 20: 780–795, 1984), and then were transferred to the SF-WME supplemented with the various tripeptides of formula (I). For each group of experiments, hepatocytes from three or four livers were used.

Statistics

Significances are calculated using Student's t-test. Values are expressed as mean ±SD.

Analyses of the Tripeptides in Hepatocytes:
   Method: (Hepatocytes in suspension)
   Plasma sample: Precipitation with trichloracetic acid.
   Centrifugation and aliquot of supernatant to HPLC.
   Ion exchange column: Nucleosil C18 (250×4.6 mm).
   Buffer TEAP 0.1%/CH$_3$CN, 1 ml/min
   Readings at 210 nm
   Testing conditions of the tripeptides
   20 μg/24 h/10$^6$ cells
   10$^6$ cells/ml
   Reduce substance to 10 μg/ml and 1,0 μg/ml
   Each substance of each concentration will be analysed 10 times during 24 h (1 h, 2 h, 4 h, 6 h, 8 h, 10 h, 12 h, 16 h, 20 h, 24 h).

Results

The following half-life values were obtained:

| Tripeptide | T½ (h) |
|------------|--------|
| N,N-Diethyl-Ile-Ile-ProNH$_2$ | 3.4 |
| N-Isopropyl-Ile-Ile-ProNH$_2$ | 2.6 |
| N,N-Diethyl-Gly-Ile-ProNH$_2$ | 2.8 |
| N,N-Diethyl-Ile-Phe-ProNHEt | 4.5 |
| H-Gly-Phe-Pro-OH | 0–1 |

6. Animal Models a) Introduction

There are no animal models for Alzheimer's disease. The transgenic mouse model is only of limited use as far as behavior is concerned. Therefore we present a battery of three rat models. Each model reproduces one of the physiopathologic features of the disease:neurofibrillary degeneration in the vincristine model, degeneration by beta-amyloid in the Gp120 model, and apoptosis in the dexamethasone model.

Vincristine is an anticarcinogen that is used as a synchronizing agent. This molecule binds to the spindle of microtubules, thus blocking the cellular multiplication during the metaphase. It is a spindle poison. The neurons do not multiply under physiologic conditions, but the axons are made of neurofibrils whose structure is similar to the one of the microtubules of the spindle. Vincristine binds to these neurofibrils thus causing peripheral neural conduction disorders in patients who are treated for neoplasm. These effects mainly affect the white matter of the axons. As vincristine does not pass the blood-brain barrier it has to be given by intracerebroventricular administration. The repeated ICV administration of vincristine causes a degeneration of the conduction pathways with the appearance of abnormal neurofibrils similar to those observed in Alzheimer's disease. This degeneration mainly affects the periventricular structures. The hippocampi are affected through a decrease of their ramifications, while the cell bodies of the neurons are not altered. We also showed that the repeated administration of vincristine is only possible for a short time (5 days at a maximum). After this period, a protective layer forms on the glia cells that prevent the diffusion of vincristine from the CSF to the neighboring nerve cells. There is no spontaneously developing Alzheimer's disease in rats that would show the different types of degenerative lesions (beta-amyloid plaques, neurofibrillary and vacuolar degeneration). ICV administration of vincristine, which may cause neurofibrillary degeneration, may be used as a partial animal model of this disease. The studies that we conducted on rats in our laboratory showed a decrease of hippocampal arborization. After the administration of vincristine, the learning ability of the animals is diminished, while a neurofibrillary degeneration of the hippocampus is observed. As it is difficult to evaluate this degeneration in a screening model, the only evaluation parameters are the learning capacities. This model has been standardized and validated in our laboratory to obtain a good reproducibility.

Dexamethasone is a corticoid similar to natural cortisol. Stress causes a release of catecholamine and cortisol (corticosterone in rats). Repetitive stress—"chronic stress"—leads to a down regulation of the hippocampal receptors to glucocorticoides. These studies, which first started in rats, were confirmed in human beings, where a specific form of depression (Golf war syndrome) is observed at first, then followed by an irreversible impairment of cognitive capacities. MRI studies on human beings showed a degeneration of the hippocampal neurons. A similar syndrome is observed in diseases associated with hypercorticism (Morbus Cushing) or during long-term corticoid treatment (Multiple Sclerosis). In rats, the repeated administration of dexamethasone first causes a down regulation of the type II receptors of the hippocampus that is followed by a degeneration of the neurons of the CAII and CAIII layers. The learning ability of the animals is impaired. This model has been standardized and validated in our laboratory to obtain a good reproducibility.

Gp120 is a surface glycoprotein of the HIV virus. This glycoprotein plays a fundamental role in the binding of the virus and the passage of viral RNA in the host cell. Isolated Gp120 also binds to CD4 receptors of the cells and causes a lesion of the membranes with the appearance of the pores into which the calcium ions dive, thus causing cellular apoptosis. On the surface of the cells Gp120 forms a deposit of glycated proteins that are quite similar to the beta-amyloid deposits. The HIV virus does not pass the blood-brain barrier, but the virally infected macrophages pass it easily. Once arrived in the CNS, the macrophage dies and releases its cellular contents with the Gp120 and other viral constituents. This Gp120 binds to the CD4 of the glia cells and also to the neurons, thus causing complex dementia as the final stage of AIDS. The observed lesions are similar to those of Alzheimer's disease, but a different distribution. In Alzheimer's disease the cholinergic structures of the nucleus of the basis and the limbic system are the first altered, whereas in complex dementia of AIDS the distribution of the plaques is general. We have conducted several rat studies using this Gp120 model. The administration into the cecerebrospinal fluid causes an important decrease of the neurons in the hippocampi associated with a decrease in the regional consumption of glucose and a decrease in blood flow. The degeneration is observed in the CAII and CAIII layers of the hippocampus that induces an impairment of the learning capacities. This model has been standardized and validated in our laboratory to obtain a good reproducibility.

b) Materials and Methods

Animals 70 male Wistar rats (Charles River, Saint Aubin les Elbeuf, France), each weighing on average 280–300 grams, are used in this animal experiment. For a period of one week, the animals were placed in stablings in an animal laboratory where the following parameters were controlled:

day/night rhythm: 7.00 a.m./7.00 p.m.

temperature: 22+/−1° C.

hygrometry: 50+/−10%

The animals got drinking water and a standard feed UAR A03 ad libitum.

Vincristine Model

The rats were slightly anesthetized by ether, an incision was made into the skin of the skull, and the skull was pierced by means of a dental burr. A metal needle was stereotaxically directed to the lateral ventricle, and then fixed by means of dental cement. Every day of the experiment, the patency of the needle was controlled.

Three days after introducing the needle (recovery from the postoperative shock) the non-anesthetized animals were injected 5 μl of normal saline with vincristine in a dose of 5 μg/kg/day. (The laboratory experiments showed that the degeneration depended on the dose of vincristine; the dose of 5 μg/kg/day causes a 40 to 60% loss of the hippocampal arborization). This administration was repeated every day for a period of five days.

Three days after the last administration of vincristine, the animals were chloralized (360 mg/kg), and, starting at the external carotid artery, a permanent floating catheter was retrogradely introduced into a common carotid artery. This catheter left again on the top of the skull, and was fixed by means of dental cement. After two days the animals had recovered from the postoperative shock. The model validation experiments demonstrated that the degeneration was particularly important after the first administration of vincristine as well as during the first days following the last administration. The steady state was reached on Day 3 after the last administration, and the model was stable for a period of several months. Once this lapse of time passed, a second type of degeneration was observed that affects the white matter, and was certainly due to apoptosis phenomena).

Five days after the last administration of vincristine, the twenty rats were randomly divided into two groups of 10 animals each:

one group of 10 rats received an intracarotid injection of 1 ml/kg/day of normal saline (controls) for a period of 10 days.

one group of 10 rats received 20 mg/kg/day of HCl-Gly-Phe-ProNH$_2$ dissolved in normal saline for a period of 10 days.

The injections were given at 9.00 a.m.

During the last five days of treatment, the rats were placed under the common learning conditions of the three models between 10.00 a.m. and 11.00 a.m. (see below).

Dexamethasone Model 20 rats were orally administered 50 mg/kg/day of dexamethasone over a period of 21 days. At Day 19, the animals were chloralized (360 mg/kg), and a catheter was placed into the carotid artery as described above. At Day 21, the animals were randomly divided into two groups:

one group of 10 rats received an intracarotid injection of 1 ml/kg/day of normal saline for a period of 10 days (controls).

one group of 10 rats received 20 mg/kg/day of HCl-Gly-Phe-PrONH$_2$ dissolved in normal saline for a period of 10 days.

The injections were given at 9.00 a.m.

During the last five days of treatment, the rats were placed under the common learning conditions of the three models between 10.00 a.m. and 11.00 a.m. (see below).

After the last learning session at 11.00 a.m., the rats were sacrificed by means of decapitation, and the hippocampi were quickly removed and put on a plate cooled to 0° C. The number of glucocorticoid receptors was determined by a binding method using a labeled corticoid and a specific inhibitor to the binding of the corticoid to the receptor (here a total agonist). The protein content was measured by Lowry's method.

The hippocampi of each rat were homogenized in 2 ml of sodium EDTA Glycerol molybdate buffer. The homogenate was centrifugated at 100.000 g for 60 minutes. An aliquot of the supernatant was diluted in distilled water, and the protein content was measured by Lowry's method. This protein concentration was between 1.3 and 1.7 mg/ml.

The rest of the supernatant was divided into three parts of 0.2 ml each. Increasing concentrations (25, 50 and 75 nmoles/ml) of dexamethasone 3H (Amersham 50 Ci/mM) were added to these parts. Three other preparations were carried out under the same conditions, while a saturating quantity of a total antagonist of the receptors (RU 28362) was added to obtain a non-specific binding of the labeled dexamethasone.

After one night of incubation at 4° C., charcoal/dextran was added to absorb the proteins and the bound dexamethasone. After centrifugation, the radioactivity of the supernatant was measured by liquid scintillation.

The radioactive quantities of the dexamethasone bound to the protein content are recorded. Results are expressed in femtomoles of the labeled corticoid bound to the receptor per mg of proteins.

Gp120 Model 30 rats are used in this experiment.

Day 0. The animals were slightly anesthetized by ether, an incision was made into the skin of the skull, and the skull was pierced by means of a dental burr. A metal needle was stereotaxically directed to the lateral ventricle, and then fixed by means of dental cement. Every day of the experiment, the patency of the needle was controlled.

Day 3. Three days after introducing the needle (recovery from the postoperative shock) the animals received an intra-ventricular injection of 10 nM/kg/day of Gp120 (dissolved in normal saline) in a volume of 20 µl. This administration was repeated daily for a period of five days.

Day 18. Ten days after the last administration of Gp120, the rats were chloralized (360 mg/kg). A permanent floating catheter was retrogradely introduced into the common carotid artery. This catheter left again on the top of the skull, where it was fixed.

Day 21. Three days later (recovery from the postoperative shock), the 30 rats were randomly divided into three group of 10 animals each:

the first group of 10 rats received an intracarotid injection of 1 ml/kg/day of normal saline for a period of 10 days.

the second group of 10 rats received 10 mg/kg/day of HCl-Gly-Phe-ProNH$_2$ (dissolved in normal saline) for a period of 10 days.

the third group received 20 mg/kg/day of HCl-Gly-Phe-ProNH$_2$ under the same conditions.

The injections were given between 9.00 and 9.30 a.m.

Day 26 to 30. The animals of all three groups were placed under the common learning conditions of the entire protocol. The learning sessions took place between 10.00 a.m. and 11.00 a.m.

Day 30. After the last learning session, the rats were sacrificed by means of decapitation, the brain was rapidly removed and frozen at 80° C. in liquid nitrogen vapor. Brain sections were made by Cryocut at −20° C.

The sections are defrosted and stained with neutral red. After fixation, the number of neurons on one slice of the hippocampus was measured. The method is standardized by counting the neurons on the same slice. An index of the number of neurons compared to a control rat allows for a more reliable quantification than the simple counting.

Learning

During the last five days of treatment, at 10.00 a.m. (1 hour after the administration of HCl-Gly-Phe-ProNH$_2$), the animals were placed into a learning cage for sound avoidance conditioning (Conditioning avoidance response). The animals learned to climb a pole first to escape from and then to avoid an electric shock. This method was standardized and quantified in our laboratory (see Le Poncin M., Lafitte J. C., Rapin J. R., Sound Avoidance Conditioning and a Mathematical approach to the description of acquisition performance, Math. Biosciences 59 (1982) 242–268).

For a period of five days, the animals were placed everyday under these learning conditions for a total of ten tests a day. Results are expressed as percentage of adequate responses, and the kinetics of the responses is represented by a multi-exponential maximum curve.

In all experiments, which we conducted in the laboratory, all control animals showed an avoidance response on Day 5 of learning (100% adequate responses).

The curve maximum represents the learning capacities. The slope of the curve evaluates the learning speed. The area under the curve (AUC) represents a good evaluation of all conditioning parameters. The maximum value of the area under the curve is 500, if the animals show 100% adequate responses as early as Day 0. In fact, an average area under the curve is calculated per day, what amounts to a maximum value of 100. In the absolute control animals, this average area under the curve is equal to 40+/−4.

In the above-mentioned experiments, the control animals are those who received just one reagent that causes degeneration. Under these conditions the optimal values of the control animals are far from being reached.

Reagents

All reagents used are grade I reagents, and are provided by Aldrich (Saint Quentin Fallavier, France).

Dexamethasone 3H is provided by Amersham (England).

The specific agonist (RU 28362) is provided by Roussel.

HCl-Gly-Phe-ProNH$_2$ was used as synthesized above.

Statistical Analysis

Results are expressed as an average with the standard error of mean (SEM) of the results obtained from ten rats par experimental group.

Following a ANOVA variance analysis, significant results are obtained by means of a Student's test.

The variability is calculated as a function of the least squares for each experimentation day. Significance is determined by a t-test.

d) Results

1. Vincristine Model

Sound Avoidance Conditioning by the Pole Climbing Test Method

The results are presented in Table I below. For each learning day, the values listed in the table correspond to the percentage of avoidance. The rat avoids getting the electric discharge by climbing the pole. On the first day, no avoidance is observed in any of the animal groups. The learning speed and capacities are significantly decreased in rats that receive vincristine as an ICV injection. The intracarotid injection treatment with HCl-Gly-Phe-ProNH$_2$ partly restores the learning parameters. This significant result is observed for the areas under the curve and for time on Day 2, 3, and 4.

Table I. Effect of HCl-Gly-Phe-ProNH$_2$ (20 mg/kg/day for a period of 10 days) on the learning capacities of rats previously treated by vincristine (5 µg/kg/day as ICV injection for a period of 5 days). The results are expressed as percentage of adequate responses.

| Treatment | D0 | D1 | D2 | D3 | D4 | AUC |
|---|---|---|---|---|---|---|
| Without vinc. | 0 | 8 +/− 2 | 34 +/− 4 | 71 +/− 4 | 90 +/− 3 | 40.6 +/− 2.3 |
| Vinc. only (controls) | 0 | 3 +/− 2 | 8 +/− 3 | 21 +/− 3 | 33 +/− 5 | 13.2 +/− 2.4 |
| Vinc. plus tripeptide | 0 | 5 +/− 2 | 20 +/− 4 | 40 +/− 5 | 59 +/− 6 | 24.8 +/− 3.2 | n = 10 by time m +/− SME,
**p > 0.01 comparison between controls and HCl-Gly-Phe-ProNH$_2$-treated animals 2. Dexamethasone Model Sound Conditioning The results are presented in Table II below, orally administered dexamethasone leads to a significant impairment of the learning capacities. HCl-Gly-Phe-ProNH$_2$ partially restores the learning capacities as soon as from the second day on. Intravenously administered HCl-Gly-PheE-ProNH$_2$ significantly restores the mean area under the curve.

Table II. Effect of HCl-Gly-Phe-ProNH$_2$ in a dose of 20 mg/kg/day for a period of 10 days on the learning capacities that were impaired by a pretreatment with orally administered dexamethasone. The results are expressed as percentage of adequate responses.

Determination of the Corticoid Receptors

The results are presented in Table III.

Table III. Determination of the type II glucocorticoid receptors in the hippocampus of rats that were pretreated by dexamethasone. The results are expressed in femtomols/mg of proteins.

| Without decam. | dexam. only (controls) | Dexam. plus tripeptide |
|---|---|---|
| 120 +/− 11 | 45 +/− 3 | **73 +/− 4 | n = 10 m +/− SME,
**p < 0.01 comparison between controls and HCL-GLY-PHE-PRONH2-treated animals The repeated administration of HCL-GLY-PHE-PRONH$_2$ reduces the down regulation of the glucocorticoid receptors in the hippocampus.

3. Gp120 Model

Sound Conditioning

The results are presented in Table IV below. Intracerebroventricular administration of Gp120 leads to an impairment of learning parameters.

Injected HCl-Gly-Phe-ProNH$_2$ restores the capacities of the animal depending on the dose. Repeated administration of 20 mg/kg is more active than the administration of 10 mg/kg. This difference is observed both quantitatively and in the learning speed parameter.

Table IV. Effect of HCl-Gly-Phe-ProNH$_2$ on the learning parameters of the rat treated by Gp120 as intracerebroventricular injection. The results are expressed as percentage of adequate responses.

| Treatment | D0 | D1 | D2 | D3 | D4 | AUC |
|---|---|---|---|---|---|---|
| Without decam. | 0 | 8 +/− 2 | 34 +/− 4 | 71 +/− 4 | 90 +/− 3 | 40.6 +/− 2.3 |
| dexam. only (controls) | 0 | 5 +/− 2 | 15 +/− 3 | 38 +/− 4 | 50 +/− 3 | 21.6 +/− 2.2 |
| Dexam. plus tripeptide | 0 | 7 +/− 2 | 29 +/− 5 | 57 +/− 4 | 75 +/− 3 | 35.0 +/− 3.1 | n = 10 by group et by time, m +/− SME,
*p < 0.05
**p < 0.01 comparison between controls and HCl-Gly-Phe-ProNH2-treated animals

| Treatment | D0 | D1 | D2 | D3 | D4 | AUC |
|---|---|---|---|---|---|---|
| Without Gp120. | 0 | 8 +/− 2 | 34 +/− 4 | 71 +/− 4 | 90 +/− 3 | 40.6 +/− 2.3 |
| Gp120. only (controls) | 0 | 6 +/− 3 | 9 +/− 3 | 12 +/− 3 | 18 +/− 3 | 11.2 +/− 2.3 |
| Gp120 plus tripeptide (10 mg) | 0 | 8/−2 | **20/−4 | **35 +/− 4 | **55 +/− 7 | **23.8 +/− 4.1 |
| Gp120 plus tripeptide (20 mg) | 0 | 8/−2 | 21/−4 | 48 +/− 5 | 70 +/− 5 | 29.6 +/− 3.0 | n = 10 m +/− SME,
*p < 0.05
**p < 0.01 comparison between controls and treated animals Neuronal Count The neurons are counted in the CAIII layers of the hippocampus. The number of neurons in one field, which in theory is always identical, is related to a theoretical value that was observed in the control animals. By definition, the value found in the control animals is 100 with a maximum variation of 5%. Table V shows the results of this neuronal count.

Table V. Counting of the hippocampal neurons after IVC administration of Gp120. Effect of the repeated injection of HCl-Gly-Phe-ProNH$_2$ in doses of 10 to 20 mg/kg.

| Controls | HCl-Gly-Phe-ProNH$_2$ 10 mg/kg/day | HCl-Gly-Phe-ProNH$_2$ 20 mg/kg/day |
|---|---|---|
| 38 +/− 3 | 46 +/− 4 | **56 +/− 2 | n = 10 m +/− SME,
**p < 0.01 comparison between controls and treated animals

Only the administration of 20 mg/kg of HCl-Gly-Phe-ProNH$_2$ leads to a significant increase in the number of neurons.

d) Discussion-Conclusion

The repeated IVC administration of vincristine causes a degeneration of the arborization of the hippocampal neurons it is, in fact, a neurofibrillary degeneration. This degeneration is more extensive, and it even affects the periventricular neurons where the vincristine diffuses. Therefore these findings are similar with those observed in the brains affected by Alzheimer's disease. The difference concerns the localization of the neurofibrillary degeneration and the affected structures.

The hippocampal structures are of particular interest to us, because their destruction leads to reduced learning performances. This is the case in this model, where the rats that receive vincristine are no longer able to learn how to avoid the electric shock by climbing the pole. It equally applies to other models, even if the degeneration is of a different type.

In the case of dexamethasone, a down regulation of the receptors takes place that precedes the phenomena of apoptosis. There is as yet no degeneration.

On the contrary, there is degeneration with Gp120, but it is not yet complete.

In all three cases, we have standardized the models to achieve recovery. If, e.g., the dose of Gp120 is doubled, or if the dose is maintained, but the treatment duration is doubled, there is almost a total degeneration. The learning parameters are next to zero, and the number of neurons is very low.

Furthermore, certain neurons do no longer retain the dye, even if they are still functional. Finally, it is still possible to stop the degeneration, if treatment is started during the progressive phase. The results that we observed do not correspond to a regrowth of neurons, but to a reduced neuronal loss.

In conclusion, directly administered HCl-Gly-Phe-ProNH$_2$ significantly improves the learning capacities, if these are impaired after ICV administration of vincristine and of Gp120, after oral treatment with dexamethasone. At the same time, the neuronal functionality of the hippocampus is improved.

The invention claimed is:

1. A method for the treatment of neurodegenerative diseases comprising administering an effective amount of a compound of formula (I) to a human patient in need thereof:

wherein X represents NH$_2$, NH—C$_{1-3}$-alkyl, or N(C$_{1-3}$ alkyl)$_2$;

R$_1$ is a residue derived from the amino acid Phe which may be optionally substituted with one or more methyl groups or one or more halogen atoms; or is a residue derived from the amino acid Ile;

R$_2$ is a residue derived from one of the amino acids Gly or Ile;

Y$_1$ and Y$_2$ independently from each other represent H or (C$_{1-3}$)alkyl;

or a pharmaceutically acceptable salt thereof.

2. The method according to claim 1, wherein X represents NH—C$_{1-3}$-alkyl, or N(C$_{1-3}$ alkyl)$_2$.

3. The method according to claim 1, wherein the neurodegenerative disease is Alzheimer's disease.

4. The method according to claim 1, wherein the neurodegenerative disease is mild cognitive impairment.

5. The method according to claim 1, wherein R$_1$ is a residue which is derived from one of the amino acids Phe which may optionally be substituted with a one or more methyl groups or one or more halogen atoms.

6. The method according to claim 5, wherein $R_1$ is a residue which is derived from Phe, which may optionally be substituted with one or more halogen atoms.

7. The method according to claim 1, wherein $R_2$ is a residue which is derived from the amino acid Gly.

8. The method according to claim 1, wherein the compound of formula (I) is glycyl-L-phenylalanyl-L-prolineamide, N,N-diethyl-isoleucyl-phenylalanyl-L-proline ethylamide, N,N-diethyl-isoleucyl-isoleucyl-prolineamide or a pharmaceutically acceptable salt thereof.

9. A pharmaceutical composition comprising one or more compounds of the following formula (I):

wherein X represents $NH_2$, $NH-C_{1-3}$-alkyl, or $N(C_{1-3}$ alkyl$)_2$;

$R_1$ is a residue derived from the amino acid Phe which may be optionally substituted with one or more methyl groups or one or more halogen atoms; or is a residue derived from the amino acid Ile;

$R_2$ is a residue derived from one of the amino acids Gly or Ile;

$Y_1$ and $Y_2$ independently from each other represent H or $(C_{1-3})$alkyl;

and pharmaceutically acceptable excipients.

10. The pharmaceutical composition according to claim 9, wherein X represents $NH-C_{1-3}$-alkyl, or $N(C_{1-3}$ alkyl$)_2$.

11. The pharmaceutical composition according to claim 9 or 10, wherein $R_2$ is a residue which is derived from the amino acid Gly.

12. The pharmaceutical composition according to claim 9, wherein the compound of formula (I) is glycyl-L-phenylalanyl-L-prolineamide, N,N-diethyl-isoleucyl-phenylalanyl-L-proline ethylamide, N,N-diethyl-isoleucyl-isoleucyl-prolineamide or a pharmaceutically acceptable salt thereof.

13. The method according to claim 1, wherein $R_1$ is a residue which is derived from Phe which is optionally substituted with one or more one or more methyl groups or one or more halogen atoms, $R_2$ is a residue derived from the amino acid Gly or Ile, and $Y_1$ and $Y_2$ independently from each other represent H or $(C_{1-3})$alkyl.

14. The pharmaceutical composition according to claim 9, wherein $R_1$ is a residue which is derived from Phe which is optionally substituted with one or more methyl groups or one or more halogen atoms, $R_2$ is a residue derived from the amino acid Gly or Ile, and $Y_1$ and $Y_2$ independently from each other represent H or $(C_{1-3})$alkyl.

* * * * *